United States Patent
Lhila et al.

[11] Patent Number: 5,498,417
[45] Date of Patent: Mar. 12, 1996

[54] TRANSDERMAL DELIVERY OF APPETITE SUPPRESSANT DRUG

[75] Inventors: Ramesh Lhila, South Windsor; Stuart Ganslaw, Simsbury, both of Conn.; Eleanor Serra, West Springfield, Mass.

[73] Assignee: Coating Sciences, Inc., Bloomfield, Conn.

[21] Appl. No.: 241,649

[22] Filed: May 12, 1994

[51] Int. Cl.⁶ .................................................. A61F 13/00
[52] U.S. Cl. ........................ 424/448; 424/449; 514/909
[58] Field of Search .................................. 424/448–449

[56] References Cited

U.S. PATENT DOCUMENTS

| | | | |
|---|---|---|---|
| 2,561,071 | 7/1951 | Prisk | 424/449 |
| 3,598,122 | 11/1972 | Zaffaroni | 424/435 |
| 3,797,494 | 3/1974 | Zaffaroni | 424/434 |
| 4,314,557 | 2/1982 | Chandrasekaran | 424/449 |
| 4,568,343 | 2/1986 | Leeper et al. | 424/449 |
| 4,645,502 | 2/1987 | Gale et al. | 424/448 |
| 4,814,168 | 3/1989 | Sablotsky | 424/78 |
| 4,818,541 | 4/1989 | Sanderson | 424/448 |
| 4,826,686 | 5/1989 | Brantl et al. | 424/448 |
| 4,834,978 | 5/1989 | Nuwayser | 424/448 |
| 5,118,692 | 6/1992 | Peck | 514/317 |
| 5,120,545 | 6/1992 | Ledger et al. | 424/449 |
| 5,164,190 | 11/1992 | Patel et al. | 424/548 |
| 5,230,896 | 7/1993 | Yeh et al. | 424/443 |

*Primary Examiner*—D. Gabrielle Phelan
*Attorney, Agent, or Firm*—Fishman, Dionne & Cantor

[57] ABSTRACT

A medical device for the transdermal delivery of an appetite suppressant drug wherein said device comprises a silicone-coated release layer, a coating containing a mixture of a pressure-sensitive adhesive, an appetite suppressant drug, a permeation enhancer and a PH control additive wherein said coated release layer is laminated to a carrier layer.

2 Claims, 1 Drawing Sheet

TRANSDERMAL DELIVERY OF APPETITE SUPPRESSANT DRUG

FIELD OF THE INVENTION

This invention relates to a medical device for delivery of a drug to the body through intact skin. More particularly, the invention relates to the transdermal delivery of an appetite suppressant drug through the skin.

BACKGROUND OF THE INVENTION

The use of transdermal patches for the delivery of drugs through the skin is well-known. For example, transdermal patches have been used to deliver drugs in all of the major therapeutic areas including, but not limited to, antibiotic and antiviral agents, analgesics, antidepressants, antihistomines, antinauseants, antispasmodics, diuretics, vasodialators, appetite suppresssants, stimulants, etc.

Although the transdermal delivery of drugs is rapidly becoming the preferred method of delivery of drugs, it is not without problems. For example, some drugs cause undesirable skin reactions, while other drugs do not readily permeate the skin. In the latter case, permeation enhancers are usually added to the drug in order to enhance the transfer of the drug through the skin; however, in some cases some drugs are difficult to use in an effective manner even when combined with a permeation enhancer. This has been found to be the case with the use of an appetite suppressant drug known as phenylpropanolamine HCL, i.e. PPA, as well as similar drugs of the same class.

It is an object of the present invention to provide a medical device for the transdermal delivery of an appetite suppressant.

It is another object of the present invention to provide an adhesive/drug combination for use in a transdermal delivery device.

It is a further object of the present invention to provide a transdermal drug delivery device for an appetite suppressant.

BRIEF DESCRIPTION OF THE DRAWING

The above and other objects and advantages of the present invention will be readily apparent from the following description with reference to the accompanying drawing wherein.

DESCRIPTION OF THE INVENTION

Figure 1:
FIG. 1 is a cross section view of the transdermal drug delivery device of the present invention.

PPA is an indirect-acting sympathomimetic amine commonly used as an anorexiant in short-term obesity therapy. In recent years, it has been found general usage as a commercially-available over-the-counter drug for diet control. While there is some literature which teaches its use in a transdermal delivery system, it is more commonly taken orally.

It is suspected that one reason PPA has not found its way into common usage in a transdermal delivery system probably stems from the fact that PPA per se does not easily permeate human skin. In fact, experimentation has shown that even in the presence of a known compatible permeation enhancer, permeation of said drug is at best marginal.

In the present invention, it has been found that PPA may be combined with a carrier adhesive and a combination of permeation enhancers to provide a transdermal delivery system which is capable of delivering approximately 72 mg. of PPA in 12 hours, i.e. 6–7 mg. PPA per hour, which is an acceptable dosage for effective use of said drug.

As seen in FIG. 1, the product or transdermal patch of the present invention is comprised of a carrier layer 10, an adhesive/drug layer 12 and a release coat or layer 14.

The carrier layer 10 of the patch may be any material which is impermeable and insoluble with respect to the adhesive/drug combination, yet flexible enough to permit application to and removal of said patch from skin without tearing or breaking. Typical materials include ethylene vinyl acetate copolymers, polyesters, polyolefins, polycarbonates, polyvinyl chlorides, copolymers of ethylene and acrylic acid, etc. In the preferred embodiment of the present invention, said carrier layer is a copolymer of ethylene and acrylic acid sold by Dow Chemical, U.S.A. as Dow Adhesive Film 821. This film is the preferred backing layer as it provides a good anchor for the adhesive/drug layer.

As should be understood, the adhesive/drug layer of the present invention is a mixture of an adhesive and PPA. The adhesive must be one that is compatible with the PPA and with human skin. Such adhesives that are known to meet this criteria are acrylic pressure-sensitive adhesives such as Gelva 788 and Gelva 737 produced by Monsanto Company and Durotak 280–2287 produced by National Starch Company. The PSA adhesive may be present in amounts of from about 25% by weight of the adhesive/drug mixture to about 90% by weight. Preferably said adhesive is present in an amount of from about 55% by weight to about 65% by weight.

The drug portion of the adhesive/drug mixture, i.e. the amount of PPA, amounts to from about 10% by weight to about 60% by weight. It has been found that amounts of from about 30% by weight to about 50% by weight are preferable.

The adhesive/drug mixture also contains a mixture of a permeation enhancer and a PH control additive which also acts as an enhancer. Said permeation enhancer may be selected from the group of compounds known as polyalkylene polyol such as polypropylene glycol, polyethylene glycol and glycenol, while said PH control additive is an alkylamine such as Trolamine 85NF produced by the Dow Chemical Company. It has been found that the PH control additive must also have permeation enhancer properties in order for the transdermal patch to be effective. Further, both the permeation enhancer and the Ph control additive/enhancer are each present in the adhesive/drug mixture in amounts of from about 0.5% by weight to about 15% by weight. Preferably, said ingredients are present in amounts of from about 3% by weight to about 4% by weight.

The final part of the transdermal patch product is the release film or layer which is removed from the product prior to use. Typically, said release layer is a silicone-coated polyester film which releasably bonds to the adhesive/drug mixture. Said release layers or films are produced by a number of companies on a commercial basis.

In addition to the above-noted components of the adhesive/drug mixture which are essential to the invention, the mixture may also contain pigments and dyes, inert fillers, processing aids such as viscosity control additive, excipients and other conventional components of transdermal devices known to the art.

The preparation of the adhesive/drug mixture is simple and straight-forward. To begin the mixing process, a predetermined amount of the adhesive is added to a Hockmeyer mixer and mixed for a predetermined period of time at 650–750 rpm. Next, the polyalkylene polyol is added to the adhesive in the Hockmeyer mixer and the speed increased to about 1750–1850 rpm. This is followed by slowly adding the drug component, i.e. PPA, to the Hockmeyer mixer and the speed thereof is increased to about 2300 rpm. Once the drug component has been added to the mixer, it is mixed for about 15 minutes and then allowed to stand for at least 6 hours before use.

One hour prior to using the adhesive/drug mixture as a coating, the standing mixture noted above is again mixed in the Hockmeyer mixer at about 1750 rpm. At this point, the PH additive/enhancer is slowly added to bring the PH to about 8.5 to 9.5 and mixed for an additional 5 minutes. A viscosity control additive such as xylene is then added to the mixture and mixed for an additional 10 minutes. The amount of viscosity control additive is that amount which is sufficient to adjust the viscosity of the adhesive/drug mixture to 2900±300 cps.

When the target viscosity is achieved, the adhesive/drug mixture is then coated onto a silicone release-coated polyester film to a thickness of about 4.5 to 6.5 mils depending upon the amount of drug component desired. It is then oven-dried to remove solvents and finally laminated to a carrier layer or backing. It has been found that a release layer of from about 1.5 mils to about 4.5 mils thickness and a carrier layer of from about 2.0 mils to about 4.0 mils thickness provide an acceptable product. The laminated product may be further processed into smaller rolls which may be further treated by die cutting and packaging as finished patches.

The following examples are offered to illustrate the product of the present invention.

Employing the mixing process noted above, two samples of the transdermal patch of the present invention were prepared. A third sample was also prepared; however, said sample did not include the combination permeation enhancer/PH control additive.

|  | SAMPLE I | SAMPLE II | SAMPLE III |
|---|---|---|---|
| ACRYLIC PSA | 58.1 | 54.4 | 62.2 |
| PHENYL PROPANOLAMINE HCL | 34.9 | 32.6 | 37.4 |
| PROPYLENE GLYCOL | 3.5 | 9.7 | — |
| TROLAMINE N.F. | 3.5 | 3.3 | — |
| GLYCERINE | — | — | 0.4 |

SAMPLES I and II were coated to a thickness of about 5.5 mils on a silicone release-coated polyester film having a thickness of 2 mils and then the coated film was laminated to a film of low density polyethylene having a thickness of 3 mils. SAMPLE III was coated to a thickness of about 5.0 mils on a silicone release-coated polyester film having a thickness of 3 mils and then was laminated to a foil/polyethylene composite film having a thickness of 2 mils.

An in vitro skin penetration study was conducted following application of the three sample formulations to excised abdominal skin preparations from human subjects using Franz-type diffusion cells. For dosage purposes, each sample PPA patch was clamped in place in the Franz-type cells so as to expose an area of 0.279 sq. in. of skin. Effluent from each Sample experiment was analyzed utilizing a high-performance liquid chromatograph (HPLC) method for PPA content. Calculations were made for the total milligrams of applied PPA which penetrated per sq. in. skin surface for both interval and cumulative data. The rate of penetration of PPA is expressed in $mg/in^2/hour$. The results of each Sample are as follows:

SAMPLE I

| COLLECTION INTERVAL (hrs.) | MEAN PPA LEVEL ($mg/in^2$) |
|---|---|
| SUMMARY OF INTERVAL DATA | |
| 0–4 | 24.44 |
| 4–8 | 3.87 |
| 8–12 | 1.61 |
| 12–24 | 2.53 |
| SUMMARY OF CUMULATIVE DATA | |
| 0–4 | 24.44 |
| 4–8 | 28.31 |
| 8–12 | 29.92 |
| 12–24 | 32.44 |

SUMMARY OF RATE OF PENETRATION DATA

| COLLECTION INTERVAL (hrs.) | ELAPSED TIME (hrs) | MEAN PPA LEVEL ($mg/in^2$) |
|---|---|---|
| 0–4 | 4 | 6.11 |
| 4–8 | 4 | 0.88 |
| 8–12 | 4 | 0.40 |
| 12–24 | 4 | 0.21 |

SAMPLE II

| COLLECTION INTERVAL (hrs.) | MEAN PPA LEVEL ($mg/in^2$) |
|---|---|
| SUMMARY OF INTERVAL DATA | |
| 0–4 | 22.90 |
| 4–8 | 3.96 |
| 8–12 | 1.62 |
| 12–24 | 2.79 |
| SUMMARY OF CUMULATIVE DATA | |
| 0–4 | 22.90 |
| 4–8 | 26.86 |
| 8–12 | 28.48 |
| 12–24 | 31.27 |

SUMMARY OF RATE OF PENETRATION DATA

| COLLECTION INTERVAL (hrs.) | ELAPSED TIME (hrs) | MEAN PPA LEVEL ($mg/in^2$) |
|---|---|---|
| 0–4 | 4 | 5.72 |
| 4–8 | 4 | 0.99 |
| 8–12 | 4 | 0.40 |
| 12–24 | 12 | 0.23 |

SAMPLE III

| COLLECTION INTERVAL (hrs.) | MEAN PPA LEVEL ($mg/in^2$) |
|---|---|
| SUMMARY OF INTERVAL DATA | |
| 0–4 | 0.030 |
| 4–8 | 0.055 |
| 8–12 | 0.119 |
| 12–24 | 0.628 |

-continued

SUMMARY OF CUMULATIVE DATA

| | |
|---|---|
| 0–4 | 0.030 |
| 4–8 | 0.085 |
| 8–12 | 0.203 |
| 12–24 | 0.832 |

SUMMARY OF RATE OF PENETRATION DATA

| COLLECTION INTERVAL (hrs.) | ELAPSED TIME (hrs) | MEAN PPA LEVEL (mg/in$^2$) |
|---|---|---|
| 0–4 | 4 | 0.007 |
| 4–8 | 4 | 0.014 |
| 8–12 | 4 | 0.030 |
| 12–24 | 12 | 0.052 |

From the above data, it is clear that the patches of SAMPLES I and II have a significantly higher skin penetration rate than the patch of SAMPLE III. Accordingly, if one is required to deliver approximately 72 mg of PPA in a 12-hour period (6–7 mg PPA per hour), said patch for SAMPLE I would have to be at least 5.83 inches in diameter, the patch for SAMPLE II would have to be at least 5.41 inches in diameter and the patch for SAMPLE III would have to be 21.32 inches in diameter.

While this invention has been described in detail with particular reference to certain preferred embodiments, it will be understood that variations and modifications may be effected without departing from the spirit and scope of the invention as defined in the appended claims.

What is claimed is:

1. An adhesive/drug mixture for use in a transdermal patch, said adhesive/drug mixture comprising a pressure-sensitive acrylic adhesive, present in an amount of from about 25% by weight to about 90% by weight, an indirect-acting phenyl propanolamine, present in an amount of from about 10% by weight to about 60% by weight, a propylene glycol permeation enhancer and a triethanolamine PH control additive which also acts as a permeation enhancer, each being present in amounts of from about 0.5% by weight to about 15% by weight.

2. A transdermal patch for delivering a drug through human skin, said patch comprising a silicone-coated release layer, an adhesive/drug mixture coating on said release layer and a carrier film laminated to said coated release layer, said adhesive/drug mixture including from about 25% by weight to about 90% by weight of a pressure-sensitive acrylic adhesive, from about 10% by weight to about 60% by weight of an indirect-acting phenyl propanolmine, a propylene glycol permeation enhancer and a triethanolamine PH control additive which also acts as a permeation enhancer wherein each is present in amounts of from about 0.5% by weight to about 15% by weight.

* * * * *